United States Patent
Muth et al.

(10) Patent No.: US 8,088,316 B2
(45) Date of Patent: Jan. 3, 2012

(54) METHOD FOR PERFORATING NONWOVEN FABRIC

(75) Inventors: Mathias Muth, Wiesbaden (DE); Indra Roy, Eggenwill (CH); Ralf Sodemann, Peine (DE)

(73) Assignee: Fiberweb Corovin GmbH, Peine (DE)

( * ) Notice: Subject to any disclaimer, the term of this patent is extended or adjusted under 35 U.S.C. 154(b) by 1310 days.

(21) Appl. No.: 11/671,185

(22) Filed: Feb. 5, 2007

(65) Prior Publication Data

US 2008/0014408 A1    Jan. 17, 2008

Related U.S. Application Data

(62) Division of application No. 10/481,939, filed as application No. PCT/EP02/07343 on Jul. 3, 2002, now abandoned.

(30) Foreign Application Priority Data

Jul. 3, 2001    (DE) .............................. 201 21 445 U

(51) Int. Cl.
  *B28B 1/48*     (2006.01)
  *B32B 3/10*     (2006.01)
  *D04H 3/08*     (2006.01)

(52) U.S. Cl. ......... 264/156; 428/131; 442/387; 425/290
(58) Field of Classification Search .................. 264/156
  See application file for complete search history.

(56) References Cited

U.S. PATENT DOCUMENTS

| | | | |
|---|---|---|---|
| 4,758,297 A | 7/1988 | Calligarich | |
| 4,886,632 A | 12/1989 | Van Iten et al. | |
| 5,573,719 A * | 11/1996 | Fitting | 264/129 |
| 5,830,555 A | 11/1998 | Srinivasan et al. | |
| 6,739,024 B1 * | 5/2004 | Wagner | 28/106 |
| 2003/0085213 A1 * | 5/2003 | Burckhardt et al. | 219/243 |

FOREIGN PATENT DOCUMENTS

| | | |
|---|---|---|
| DE | 198 27 567 A | 12/1999 |
| DE | 198 56 223 A1 * | 6/2000 |
| DE | 198 56 223 B4 | 5/2004 |
| EP | 0 472 992 B1 | 5/1996 |
| EP | 1 048 419 A | 11/2000 |
| GB | 2 267 680 A | 12/1993 |
| JP | 02 216252 A | 8/1990 |
| JP | 2-216252 A * | 8/1990 |
| JP | 06-280150 A | 10/1994 |
| JP | 6-280150 A * | 10/1994 |
| WO | WO 99/65673 A1 | 12/1999 |

* cited by examiner

*Primary Examiner* — Christina Johnson
*Assistant Examiner* — Patrick Butler
(74) *Attorney, Agent, or Firm* — Alston & Bird LLP

(57) ABSTRACT

The present invention relates to the perforation of nonwovens with a perforating roll and an opposing roll. The perforating roll and opposing roll form a gap, through which a nonwoven being perforated, is guided and perforated. The perforation apparatus comprises a feed device and a withdrawal device. The feed device is arranged such that the nonwoven being perforated advances first onto the opposing roll, before it enters the gap. The withdrawal device is arranged such that after leaving the gap, the perforated nonwoven remains on the perforating roll. Furthermore, a perforation method and a corresponding nonwoven structure are provided.

16 Claims, 3 Drawing Sheets

METHOD FOR PERFORATING NONWOVEN FABRIC

CROSS-REFERENCE TO RELATED APPLICATIONS

This application is a divisional of U.S. application Ser. No. 10/481,939, filed Jun. 4, 2004 now abandoned, which is a national phase entry from PCT/EP2002/07343, filed Jul. 3, 2002, claiming priority from German Application No. 20121445.8, filed Jul. 3, 2001, all of which are hereby incorporated herein by reference.

FIELD AND BACKGROUND OF THE INVENTION

The present invention relates to the perforation of nonwovens with a perforating roll and an opposing roll, and as well as products that include such nonwovens.

The perforation of nonwovens has advantages, when it comes to fields of application, such as absorption of liquids or particles. For example, U.S. Pat. No. 5,858,504 discloses a production method, a production apparatus, as well as a nonwoven, which is perforated. The production method provides for perforating a nonwoven by means of a needle roll and a roll with apertures that is arranged in facing relationship with the needles. To this end, the apparatus comprises two arrangements of rolls in an S-shaped configuration. The S-shaped arrangements of rolls operate differently fast, so that because of the speed difference the nonwoven fabric advancing through the two S-shaped roll arrangements is drawn before being perforated. After the perforation, the perforated nonwoven remains on the opposing roll and advances to the second S-shaped arrangement of rolls. Both the opposing roll and the needle roll are unheated, so that the nonwoven is perforated below the melting point of the used polymer.

SUMMARY OF THE INVENTION

It is an object of the present invention to provide a perforating apparatus for nonwovens, a method for perforating a nonwoven, a nonwoven, as well as a product including such a nonwoven, with the aim of stabilizing perforations for applications and further processing operations.

An apparatus for perforating nonwovens according to the invention comprises a perforating roll and an opposing roll. The perforating roll and the opposing roll form a gap through which the nonwoven is advanced and perforated. Furthermore, the apparatus for perforating nonwovens comprises a feed device and a withdrawal device. The feed device is arranged such that a nonwoven being perforated advances first onto the opposing roll, before it enters the gap. The withdrawal device is arranged such that after leaving the gap, the perforated nonwoven remains on the perforating roll, preferably for a certain period of time.

Preferably, the perforating roll is a needle roll. The needles have in particular a concentric diameter. Besides that, the needles may also have different diameter geometries. For example, they may be star-shaped, rectangular, or half angles. According to a further development, it is provided that a nonwoven that is to be perforated, loops the opposing roll at an angle of at least 45°, preferably at a looping angle greater than 90°. Furthermore, it is preferred that a perforated nonwoven loops the perforating roll at an angle of at least 45°, preferably at an angle greater than 90°.

A further development provides that the perforation apparatus for nonwovens has a heating system for the nonwoven that is to be perforated.

Another further development provides between the feed device of the nonwoven and the opposing roll for a defined adjustment of the tension, which acts upon the nonwoven. An additional development provides that between the perforating roll and the withdrawal device of the nonwoven, the perforation apparatus for the nonwovens permits a defined adjustment of the tension, which acts upon the perforated nonwoven. Preferably, a greater tension of the nonwoven is adjusted between the feed device and the opposing roll than a tension that is effective between the perforating roll and the withdrawal device of the nonwoven.

A particularly independent concept thereof provides that a method for perforating a nonwoven is made available, wherein the nonwoven advances from a feed device into a gap between a perforating roll and an opposing roll, wherein the nonwoven is perforated in the gap, and advanced to a withdrawal device after the perforation, and wherein the nonwoven loops, before being perforated, the opposing roll at an angle greater than 45°. Between the feed device and the opposing roll the nonwoven undergoes a preliminary elongation from 1.5% to 10%, before it loops the opposing roll. The preliminary elongation step occurs in particular in the machine direction (MD), but may also occur in the cross direction (CD).

A preliminarily elongated nonwoven that advances onto the opposing roll has the advantage that it is set because of the frictional force that is effective between the opposing roll and the nonwoven. The preliminary elongation is especially advantageous because displaced fibers remain in their position as a result of a subsequent setting. This setting remains intact at least until the perforating roll with the opposing roll perforate the nonwoven. For example, an S-shaped arrangement of rolls is used as feed device of the nonwoven. Via the S-shaped arrangement of rolls, a tension is applied to the nonwoven between this feed device and the opposing roll. As a result of the frictional forces between the nonwoven and the opposing roll, the nonwoven remains in its position. This way of setting makes it possible to adjust in particular the tension that is effective between the feed device and the opposing roll and acts upon the nonwoven, independently of further devices, such as deflecting rolls, etc. that are arranged downstream of the perforating roll and the opposing roll.

Preferably after its perforation, the nonwoven loops the perforating roll at an angle of at least 45°. To this end, the nonwoven that previously advanced over the opposing roll, is deflected during the perforation or shortly before or thereafter. The setting of the nonwoven on the perforating roll, which continues over a certain rotational path of the perforating roll, leads to a further stabilization of the perforations in the nonwoven itself. Preferably, the nonwoven loops the perforating roll at an angle between 90° and 270°.

According to a further concept of the invention, a nonwoven is produced with the perforation apparatus or by a method as described in the foregoing. The nonwoven includes perforations that are approximately circular. In particular, the perforations have a ratio of axes MD to CD that is approximately 1, preferably 1 to 1.18. Preferably, such a nonwoven is used in a product, with the nonwoven comprising stabilized, funnel-shaped apertures on a product surface. These apertures originate from the perforations that are realized during the perforation process or in the perforation apparatus for nonwovens.

Such a perforated nonwoven can be used in particular in products, which are used in the field of hygiene. These may include diapers, sanitary pads, incontinence articles, or others. Such a nonwoven is likewise used as component of a product in the case of medical articles, such as coverings, protective garments, parts thereof, as well as in the household area, for example, in wipes. Furthermore, the nonwoven is usable anywhere, where on the one hand defined hole sizes are preferred, and where on the other hand such characteristics are important, as absorption of liquids or adsorption of particles. For example, the surface of the nonwoven may be made hydrophilic, for example, by means of applying additives or a coating. Likewise, the nonwoven in use may be charged electrostatically. Furthermore, the nonwoven may be single-layered or multilayered, or form a laminate with a film or other substrates. In particular, it is also possible to use such a material in areas, where only certain regions are to be permeable to liquids and vapor.

Examples of materials that are advantageous to perforate are shown in the following table for at least two-layered materials:

| Material of the second layer | Material of the first layer |
|---|---|
| Spunbonded PP | Spunbonded PE |
| Carded PP | Spunbonded PE |
| Spunbonded PP | Spunbonded BICO, e.g., PP/PE |
| Spunbonded PP | Carded BICO, e.g., PP/PE, preferably with PET (for example, from 10% to 40%) |
| PP film | PE film |
| Nonwoven PP | PE film |
| Spunbonded PP/PE BICO | Spunbonded PE |
| Spunbonded PP/PE BICO | PE film |
| Nonwoven PP | High-bulk nonwoven PP/PE BICO |
| Spunbonded HDPE | Carded BICO, e.g., PP/PE, preferably with PET (for example from 10% to 40%) |
| Nonwoven PP | Carded PE |
| Nonwoven PP | Nonwoven PP with low melting point, for example, Softspun ™ |
| Spunbonded PP/PE BICO | Carded PP/PE BICO |

The weights per unit area were tested, as follows:

| Weight per unit area of second layer [gsm] | Weight per unit area of first layer [gsm] |
|---|---|
| From about 10 to about 50 | From about 10 to about 50 |

Preferably the first layer has a weight per unit area that is higher than the weight per unit area of the second layer.

| Sample | Weight per unit area [g/m$^2$] | Elongation rate [%] | Ratio of Axes MD/CD | Hole surface [mm$^2$] | Open Surface [%] |
|---|---|---|---|---|---|
| A | 43 | 2.8 | 1.01 | 1.5 | 22.3 |
| B | 43 | 1.7 | 1.13 | 1.46 | 22.4 |
| C | 30 | 2.2 | 1.04 | 1.38 | 21.1 |
| D | 25 | 5.6 | 1.11 | 1.31 | 20.7 |
| E | 30 | 3.5 | 1.16 | 1.24 | 18.9 |

Where:
Elongation rate: Ratio of the material width directly upstream of the gap to the width of the original material in percent
Ratio of axes: Average ratio of the longitudinal axis to the transverse axis of the holes, when assuming an ellipsis with MD=machine direction and CD=cross direction
Hole surface: Average surface of the holes in mm$^2$ (computed with the image processing pro-gram Image-Pro Plus Version 4.5 of MediaCybernetics)
Open surface: Average ratio of perforated surface to the total surface of the nonwoven in percent.

In all tests the penetration depth of the needles into the perforated opposing roll amounted to 2.7 mm. The used samples were nonwoven feedstock structures that were each produced as spunbonds.
Sample A: Two-layer material produced by the Docan process, with an upper layer comprising a 20 gsm nonwoven PP, and a lower layer comprising a 23 gsm nonwoven of PP/PE bicomponents;
Sample B: Same as sample A
Sample C: Single-layer 30 gsm nonwoven of PP produced by the Docan process;
Sample D: Same as C, but only 25 gsm;
Sample E: Single-layer nonwoven of PP with 30 gsm produced by the S-Tex process.

As shown in particular by the ratio of the hole sizes MD/CD, it is also possible to stabilize in particular round apertures of the perforations. The hole diameters range in MD from 1 to 1.8 mm and in CD from 0.8 to 1.7 mm. Preferably, the nonwoven has a pretension, which provides for an elongation rate between 2% and 3%.

A further influence on the hole sizes is exercised by the speed, at which the nonwoven advances through the perforation apparatus. The nonwoven advances through the perforation apparatus at speeds from 5 m/sec. to 130 m/sec. Speeds from 45 m/sec. to 120 m/sec., in particular from 60 m/sec. to 95 m/sec. were found advantageous for producing a stable perforation. In the case of hole diameters in a range below 0.5 mm, it is possible to adjust a higher operating speed. In this instance, it is possible to adjust speeds up to 200 m/sec., preferably speeds above 150 m/sec. The hole diameters will then range from 0.5 to 0.1 mm. The opposing roll has a temperature preferably from 45° C. to 95° C., in particular 55° C. to 75° C.

According to a further concept, a perforation apparatus for a nonwoven being perforated comprises a feed device, which is arranged such that the nonwoven advances over the opposing roll with a looping angle above 120°, preferably above 150°, before it is possible to perform a perforation. With that, it is accomplished in particular that in the presence of a preheated opposing roll, the structure is supplied to the perforating roll in a preheated state. Moreover, as a result of the looping, a tension in the material decreases as it is in contact with the opposing roll, thereby achieving an especially stable perforation.

According to a further embodiment, the opposing roll comprises a coating, preferably a rubber coating. In particular, the coating has a thickness from 1.5 mm to 15 mm, in particular at least 4 mm. The elevations of the perforating roll can penetrate the coating, preferably as deep as from about 2.5 mm to about 6 mm.

According to one embodiment, an integrated production process is used for producing a two-layer laminate that is to be perforated. For example, in the production of a nonwoven, a spunbonding machine with one or more spin beams is made available. One of the spin beams is used to produce, for example, a polymer blend with a low melting point, and a second spin beam serves to produce a PP/PE BICO nonwoven. Furthermore, it is also possible to apply a second layer to a prefabricated material, and to subsequently perforate it. Furthermore, there is the possibility of producing the first and the second layer inline and to perforate them in a separate process step. As shown by the example of a nonwoven fabric, there further exists the possibility of using combinations of film and nonwoven materials. For example, it is possible to extrude a film on, for example, a carded nonwoven, and to supply them subsequently to a perforation unit.

According to a further embodiment, the fibers of the first layer are blended at least in part with fibers of a nonwoven material of the second layer, in particular in the form of an entanglement. For example, while two separately produced nonwoven layers may have between them a boundary of materials, the two partially intermixed nonwoven layers exhibit a transition of materials. Beyond the transition of materials, the one and the other layer comprise respectively only one thermoplastic material. Such a structure is produced in particular by an inline process. Preferably, the perforated structure comprises a phase transition, or according to a further embodiment, for example, a complete blending of the fibers at least in part in the region of the perforation. Preferably, the first and the second layer are produced in the same manner. Both layers are, for example, extruded nonwovens, which are produced on the same machine. There also exists the possibility that different materials with respectively different properties can be combined to one perforated structure. Whereas the one nonwoven contains at least predominantly PP, the other nonwoven consists for the most part of HDPE or DAPP. Moreover, there exist possibilities of combining different methods of producing nonwovens, in particular using high-bulk staple fiber nonwovens with spunbonds or also a melt blown nonwoven with spunbonds, as well as further combinations.

Examples for an application of the laminate or structure in a product include hygienic products, sanitary and household products, in particular, wipes, medical products, surface applications in products, filter materials, protective garments, geotextiles, and disposable products.

BRIEF DESCRIPTION OF THE DRAWINGS

While further advantageous embodiments and further developments become apparent from the attached drawing, they are not intended to limit the invention in its realization. The therein illustrated features and further developments are also combinable with those described above to embodiments of the invention that are otherwise not described in greater detail.

In the drawing.

DETAILED DESCRIPTION

Figure 1:
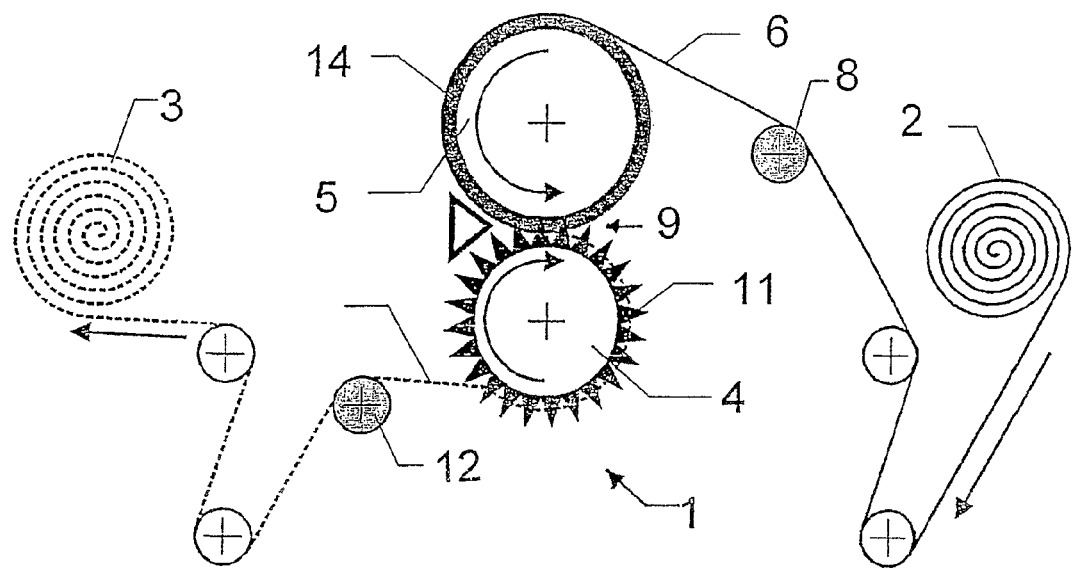
FIG. 1 shows a perforation apparatus for nonwovens with an unwinding device and a takeup device.

FIG. 1 shows a perforation apparatus 1 for nonwovens with an unwinding device 2 and a takeup device 3. In the place of an unwinding device 2 or takeup device 3, it is also possible to provide other production stations. For example, a direct production line of nonwovens, staple fiber nonwovens and/or meltblowns may precede the perforation apparatus 1. In the place of the takeup device 3, one may provide a manufacturing machine, a festooning unit, a spraying unit, a production apparatus for a product such as a wipe cloth, or others. From the unwinding device 2, a preferably presolidified nonwoven or a laminate of one or more nonwovens or nonwovens with a different material, for example, a film, advance to a perforating roll 4. The perforating roll 4 comprises perforation means. In the present case, the perforating roll 4 is constructed as a needle roll. Arranged in facing relationship with the perforating roll 4 is an opposing roll 5. Preferably, both the perforating roll 4 and the opposing roll 5 have the same circumferential speed. A nonwoven 6 that is to be perforated and is supplied by the unwinding device 2, advances via feed rolls 7 onto the opposing roll 5. The feed rolls 7 are especially constructed such that between a feed device 8 and the opposing roll 5, it is possible to adjust a definable tension of the nonwoven 6 that is to be perforated. Preferably, the feed device 8 comprises a tension measuring roll. Advancing from the feed device 8, the nonwoven 6 comes to lie on the opposing roll 5 such that it loops the latter at least in part. Preferably, the opposing roll 5 is directly heated. In particular, the temperature of the opposing roll 5 is such that it is below the softening or melting point of the used polymer of the nonwoven 6 that is to be perforated or the used laminate. Preferably, such a tempering is transferred by the opposing roll 5 while entraining the nonwoven 6 that is to be perforated. Furthermore, there is the possibility that heating devices not shown in greater detail heat the nonwoven before its perforation. In this process, it is attempted to accomplish that the nonwoven assumes a temperature, which is below the melting point of the used polymer. From the opposing roll 5, the nonwoven 6 being perforated advances into a gap 9, which is formed by the perforating roll 4 and the opposing roll 5. In the gap 9, the nonwoven 6 to be perforated is perforated and transferred in accordance with this perforation apparatus 1 to the perforating roll 4. From the perforating roll 4, the needles 11 of the perforation apparatus 1 advance a perforated nonwoven 10 to a withdrawal device 12. As shown, additional withdrawal rolls 13 are arranged downstream of the withdrawal device 12. Preferably, the withdrawal device 12 comprises a tension measuring roll. From the withdrawal rolls 13, the perforated nonwoven 10 advances to the takeup device 3. Preferably, the perforated nonwoven 10 is subjected to a tension that is lower than the tension acting upon the nonwoven 6 that is to be perforated. On the perforating roll 4, the perforated nonwoven 10 advances along a certain looping angle. In this manner, the perforation stabilizes in the nonwoven. Preferably, the perforations are stabilized in addition by applying via the withdrawal device 12 in a corresponding manner a tensile force to the nonwoven 10 advancing between the withdrawal device 12 and the perforating roll 4. Furthermore, the perforating roll 4 may also be tempered. The heat supply to the perforated nonwoven 10 or the corresponding laminate stabilizes the fibers of the nonwoven that are displaced in this manner.

According to a further embodiment, the temperature of the opposing roll 5 is at least 40° C. higher than that of the perforating roll 4. A further embodiment provides that the opposing roll is tempered, whereas the perforating roll 4 is not. Rather, the latter may also be cooled, for example, to a temperature of about 18° C. and lower.

Figure 2:
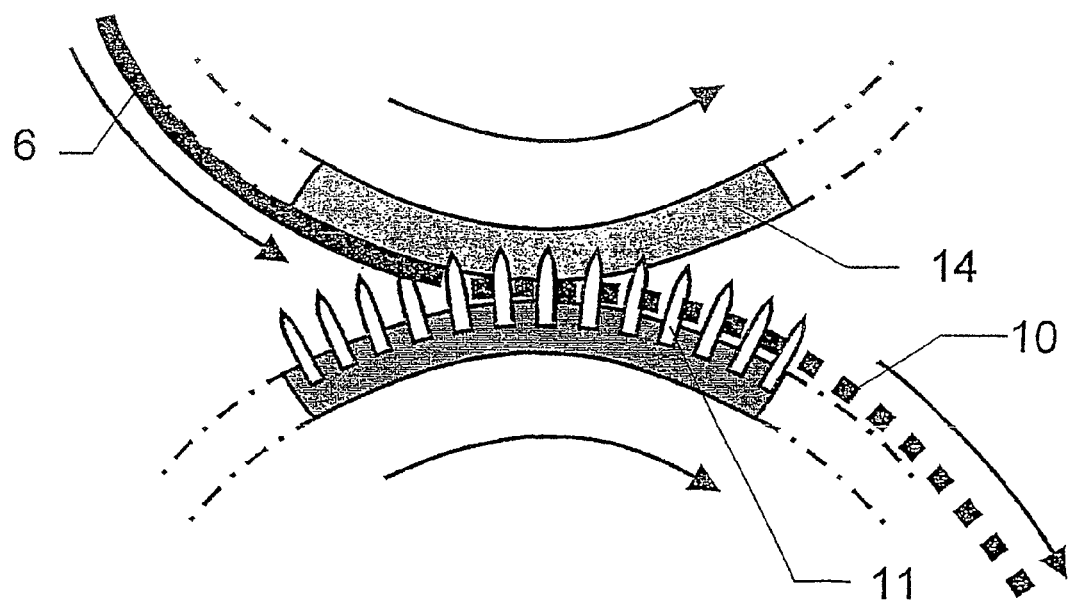
FIG. 2 is a cutout view of FIG. 1, which shows a transfer of the layer the nonwoven that is to be or has been perforated, from an opposing roll to a perforating roll of the perforation apparatus.

FIG. 2 is a cutout view of FIG. 1 that shows in greater detail the perforating roll 4, the opposing roll 5, as well the nonwoven 6 to be perforated, which becomes the perforated nonwoven 10. Components of the perforating roll 4 engage the opposing roll 5. As a result of this engagement, the nonwoven that enters the gap formed between the opposing roll 5 and the perforating roll 4 undergoes a perforation. Preferably, the perforation occurs by displacing the fibers of the nonwoven. As a result, the fiber structure remains intact at least on the surface of the nonwoven. In particular, the fibers are only displaced, without being premelted or softened. As a result, the properties of the fibers, such as, for example, a preferred drainage of liquids along a fiber, thus remain unchanged. By transferring the nonwoven from the opposing roll 5 to the perforating roll 4, the perforations as such are maintained in a stabilized state. In this case, the needles 11 penetrate the nonwoven. Preferably, the needles 11 also penetrate a coating 14 of the opposing roll 5. Likewise, the coating 14 itself may comprise holes, which are arranged in facing relationship with the needles.

Figure 3A:
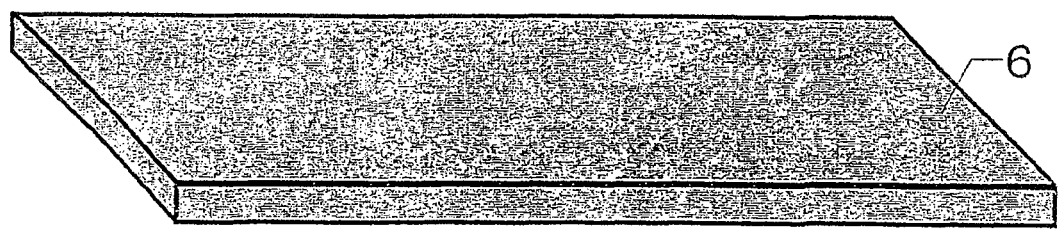
FIGS. 3a-b show a single layer material that is to be perforated.
Figure 3B:
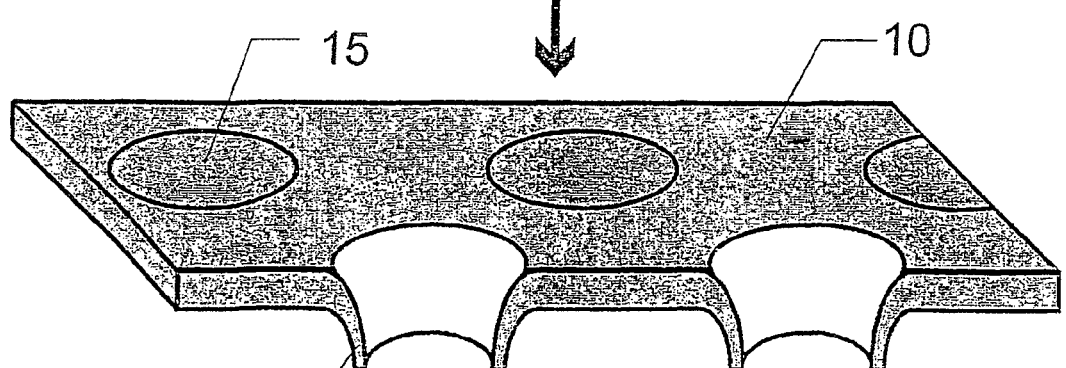

FIGS. 3a and 3b show a single-layer nonwoven. Whereas FIG. 3a shows the nonwoven 6 that is to be perforated, FIG. 3b shows the perforated nonwoven 10. As can be noted from FIG. 3b, the perforations 15 may be conical. The type of perforation stabilizes conical structures 18, so that these project as elevations from the bottom of the nonwoven.

Figure 4A:
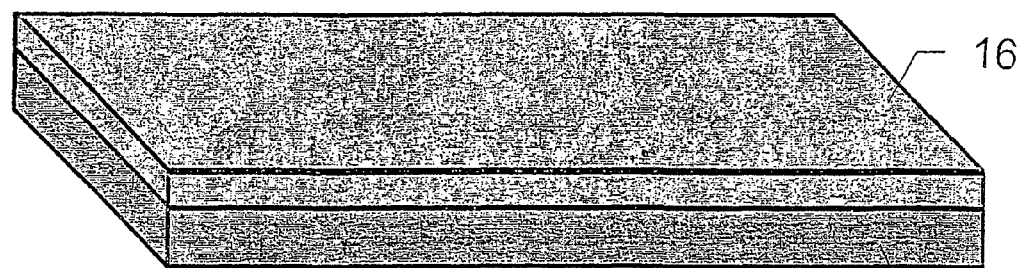
FIGS. 4a-b show a two-layer material that is to be perforated.
Figure 4B:
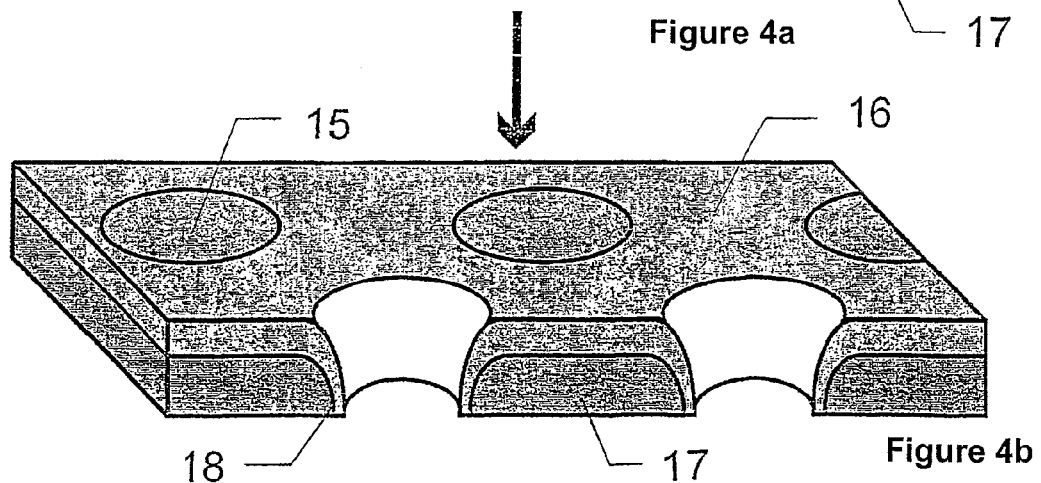

FIGS. 4a and 4b show a perforation of a two-layer material, with a first layer 16 being a nonwoven. A second layer 17 may be a nonwoven or a different material. For example, the second layer may be a film. It is also possible that the first layer 16 and the second layer 17 are different or identical types of a nonwoven. The first layer 16 includes perforations 15, which extend as conical structures 18 into the second layer 17. Preferably, the structures 18 are shaped such that they do not project from the surface of the second layer 17. Preferably, the layer 17 forms approximately completely the surface without material of the first layer 16. According to a further development, the two-layer material may also have from one funnel-shaped structure 18 to the next funnel-shaped structure 18 a slight undulation at least on that side, toward which the funnel-shaped structures 18 rise. The opposite side, however, is preferably level.

The invention claimed is:

1. A method of perforating a nonwoven, comprising
   advancing a nonwoven from a feed device to a gap between a perforating roll and an opposing roll, wherein the opposing roll is heated to a temperature that is at least 40° C. higher than that of the perforating roll;
   as the nonwoven enters the gap, directing the nonwoven to loop the opposing roll at an angle greater than 45°;
   between the feed device and the opposing roll, preliminarily elongating the nonwoven between 1.5% and 10%, before it loops the opposing roll;
   perforating the nonwoven in the gap;
   after having been perforated, advancing the nonwoven from the gap to a withdrawal device.

2. The method of claim 1, further comprising, after the perforating step, directing the nonwoven to loop the perforating roll at an angle of at least 45°.

3. The method of claim 2, wherein the nonwoven is directed to loop the perforating roll at an angle between 90° and 270°.

4. The method of claim 1, wherein the perforating step comprises forming perforations that are approximately circular.

5. The method of claim 4, wherein the perforations have a ratio of axes in the machine direction to cross direction of from 1 to 1.18.

6. The method of claim 1, wherein the nonwoven is subjected to a level of tension between the feed device and the opposing roll that is greater than a level of tension between the perforating roll and the withdrawal device.

7. The method of claim 1, further comprising the step of frictionally setting the nonwoven as it passes between the gap such that the nonwoven is stabilized during perforation.

8. The method of claim 1, wherein the elongated nonwoven sheet material loops the opposing roll at an angle greater than 90°.

9. A method of perforating a nonwoven, comprising:
   elongating a nonwoven sheet material between 1.5% and 10%;
   looping the elongated nonwoven sheet material over a first roll at an angle greater than 45°;
   passing the elongated sheet material through a gap between the first roll and a second roll having a plurality of needles; and
   perforating the elongated sheet material as it passes through the gap, and wherein the first roll is heated to a temperature that is at least 40° C. higher than that of the second roll.

10. The method of claim 9, further comprising the step of looping the elongated nonwoven sheet material over second roll at an angle of at least 45° following the perforation step.

11. The method of claim 9, wherein the elongated nonwoven sheet material loops the first roll at an angle greater than 90°.

12. The method of claim 9, wherein the nonwoven is directed to loop the second roll at an angle between 90° and 270°.

13. The method of claim 9, wherein the perforating step comprises forming perforations that are approximately circular.

14. The method of claim 13, wherein the perforations have a ratio of axes in the machine direction to cross direction of from 1 to 1.18.

15. The method of claim 9, wherein the nonwoven is subjected to a level of tension between a feed device and the opposing roll that is greater than a level of tension between the perforating roll and a withdrawal device.

16. The method of claim 9, further comprising the step of frictionally setting the nonwoven as it passes between the gap such that the nonwoven is stabilized during perforation.

* * * * *